United States Patent
Shimojyou et al.

(10) Patent No.: US 11,409,132 B2
(45) Date of Patent: Aug. 9, 2022

(54) OPHTHALMIC LENS, METHOD FOR DESIGNING THE SAME, METHOD FOR MANUFACTURING THE SAME, AND OPHTHALMIC LENS SET

(71) Applicant: HOYA CORPORATION, Tokyo (JP)

(72) Inventors: Akira Shimojyou, Tokyo (JP); Kazuo Nakazawa, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 477 days.

(21) Appl. No.: 16/480,224

(22) PCT Filed: Feb. 2, 2017

(86) PCT No.: PCT/JP2017/003758
§ 371 (c)(1),
(2) Date: Jul. 23, 2019

(87) PCT Pub. No.: WO2018/138931
PCT Pub. Date: Aug. 2, 2018

(65) Prior Publication Data
US 2020/0004045 A1  Jan. 2, 2020

(30) Foreign Application Priority Data
Jan. 24, 2017 (JP) .............................. JP2017-009956

(51) Int. Cl.
*G02C 7/04* (2006.01)
(52) U.S. Cl.
CPC ............. *G02C 7/041* (2013.01); *G02C 7/046* (2013.01)
(58) Field of Classification Search
CPC ................................ G02C 7/041; G02C 7/046
(Continued)

(56) References Cited

U.S. PATENT DOCUMENTS

| 8,684,520 B2* | 4/2014 | Lindacher | G02C 7/028 |
| | | | 351/159.02 |
| 2009/0303433 A1 | 12/2009 | Shimojo | |
| 2010/0321632 A1* | 12/2010 | Sanger | G02C 7/044 |
| | | | 351/159.41 |

FOREIGN PATENT DOCUMENTS

| CN | 101583325 A | 11/2009 |
| JP | H05-181096 A | 7/1993 |

(Continued)

OTHER PUBLICATIONS

Mar. 11, 2020 Office Action issued in Chinese Patent Application No. 201780060795.7.
(Continued)

*Primary Examiner* — James R Greece
(74) *Attorney, Agent, or Firm* — Oliff PLC

(57) ABSTRACT

An ophthalmic lens, including: an optical portion having: a near portion with a near dioptric power for viewing near distance; and a distance portion with a distance dioptric for viewing a distance further than the near distance; with the near portion or the distance portion being centrally disposed, wherein a portion that is not centrally disposed is annularly disposed at an outer edge of the near portion or the distance portion, the near portion or the distance portion centrally disposed in the optical portion having a portion A in which power is intensified and then weakened when viewed in X direction from a center to a periphery, and having a portion A' in which power is intensified and then weakened when viewed in X' direction from the center to the periphery, which is an opposite direction to the X direction, and also included is a related technique thereof.

24 Claims, 8 Drawing Sheets

(58) Field of Classification Search
USPC .................................................. 351/159.05
See application file for complete search history.

(56) References Cited

FOREIGN PATENT DOCUMENTS

| | | |
|---|---|---|
| JP | 2006-505011 A | 2/2006 |
| JP | 2012-93522 A | 5/2012 |
| WO | 2004/042454 A1 | 5/2004 |
| WO | 2006/129707 A1 | 12/2006 |
| WO | 2013/149303 A1 | 10/2013 |
| WO | 2014/128744 A1 | 8/2014 |

OTHER PUBLICATIONS

Thibos et al.; "Modelling the impact of spherical aberration on accommodation;" Ophthalmic and Physiological Optics; 2013; pp. 482-496; vol. 33, No. 4.
Aug. 7, 2020 Extended Search Report issued in European Patent Application No. 17894633.1.
Specification, NPL. cite 1.
Jul. 30, 2019 International Preliminary Report on Patentability issued in International Patent Application No. PCT/JP2017/003758.
May 9, 2017 Search Report issued in International Patent Application No. PCT/JP2017/003758.

* cited by examiner

Power distribution of Example 2

Power distribution of Comparative Example 2

OPHTHALMIC LENS, METHOD FOR DESIGNING THE SAME, METHOD FOR MANUFACTURING THE SAME, AND OPHTHALMIC LENS SET

TECHNICAL FIELD

The present invention relates to an ophthalmic lens, a method for designing the same, a method for manufacturing the same, and an ophthalmic lens set.

DESCRIPTION OF RELATED ART

As an ophthalmic lens, for example, a contact lens, an intraocular lens, etc., are known (in this specification, a spectacle lens is excluded as an ophthalmic lens). For example, a multifocal contact lens (multifocal lens) can be given as a contact lens, which ensures near dioptric power for viewing near distance and distance dioptric power for viewing far distance, with a single lens. The configuration of this multifocal lens includes, for example, a configuration in which a near portion with a near dioptric power is centrally disposed in a lens, and a distance portion with a distance dioptric power is annularly disposed at the outer edge of the near portion in the lens (For example, [FIG. 1] [FIG. 2] of patent document 1). On the contrary, a configuration is also known in which a distance portion with distance dioptric power is centrally disposed in the lens, and a near portion with near dioptric power is annularly disposed at the outer edge of the distance portion (For example, [FIG. 12] of patent document 2).

PRIOR ART DOCUMENT

Patent Document

[Patent Document 1] Japanese Published Patent Application No. 2006-505011
[Patent Document 2] WO 2006/129707

SUMMARY OF THE INVENTION

Problem to be Solved by the Invention

Before describing the subject of the present invention, an optical portion will be described. An example of the multifocal lens is as follows: a near portion with near dioptric power is centrally disposed in the lens, and a distance portion with distance dioptric power is annularly disposed at the outer edge of the near portion (multifocal lens, also simply called a lens).

First, FIG. 1 is a schematic plan view of a conventional multifocal lens (top view when looking at a direction of the earth from a direction of the heavens in a direction of an optical axis, when the lens is placed on a horizontal base with a front surface (convex surface) of the lens facing up. The same applies to a planar view). A distance on the lens in planar view is referred to as a planar view distance. Reference numerals 1 denotes a near portion, 2 denotes a distance portion, 3 denotes an optical portion, 4 denotes a peripheral portion, and 5 denotes a multifocal contact lens. The reference numerals will be omitted hereinafter.

As shown in FIG. 1, a near portion is centrally disposed, and an annular distance portion is disposed at the outer edge of the near portion, with an optical center O of the lens being concentric. In this example, the optical center O is made to coincide with a geometric center. Thus, the optical portion having the near portion and the distance portion is configured. Further, there is an annular peripheral portion at the further outer edge of the optical portion. The peripheral portion usually has a flange shape that can easily enter the back of an eyelid when the lens is placed on a cornea. Namely, the optical portion and the peripheral portion constitute the lens of this example. However, the optical portion and the peripheral portion are each distinguished to perform the above-mentioned function, and there is not a clear visible boundary such as a step between the optical portion and the peripheral portion.

Initially, when plotting the power as viewed from the end F to the end F' in the X-X' direction (that is, a radial direction), the near dioptric power should be ensured in the near portion (N-N' region), and the distance dioptric power should be ensured in the distance region (F-N region and N'-F' region).

However, an actual lens does not necessarily have such a power plot. This is shown in FIG. 2. FIG. 2 is a diagram of plotting the power when the optical portion of a conventional multifocal contact lens is viewed from the end F to the end F' in the X-X' direction. The horizontal axis indicates a distance from the optical center O at X-X' when the lens is viewed in plan. The vertical axis indicates a lens power (unit: diopter [D]), in which the power is increased toward the upper side, and the power is decreased toward the lower side. The term "power" as used herein refers to the power provided by a difference in the shape (curvature) of both surfaces of the lens.

As shown in FIG. 2, in the case of an actual lens, when the power change is viewed in a direction from the optical center O toward the periphery (X direction; hereinafter, this direction is used unless otherwise specified), the power is decreased gradually at the beginning, then the power is decreased sharply, and decrease of the power becomes gradual again, and finally reaches a distance dioptric power.

In an example of the multifocal contact lens (multifocal lens) mentioned here, it is necessary to provide a portion where the power changes. In view of this situation, the decrease of the power when viewed in the X direction cannot but be a state as shown in FIG. 2 (or [FIG. 1] [FIG. 2] of Patent Document 1). Therefore, in the conventional lens, there is also a case where a power changing portion is positioned as a transition portion or an intermediate portion (Reference numeral 104 in FIG. 12 of Patent Document 2). In such a case, it is impossible to ensure the near dioptric power in the hatched portion of FIG. 2 (that is, the portion where the power starts to be decreased). Namely, the following situation sometimes occurs: in the portion that requires a near vision, sufficient near dioptric power cannot be ensured.

In order to prevent such a situation, as shown in FIG. 3, a position at which the power is decreased when viewed in the X direction and the X' direction, is moved away from the optical center O, as compared with FIG. 2. In this way, the near dioptric power can be ensured in the near portion (region of N-N') which is set in advance.

However, when the above method is adopted, as shown in FIG. 3, the distance portion disposed at the outer edge of the near portion is narrowed this time. Further, as a result, it is not possible to ensure the near dioptric power in the hatched portion in FIG. 3 (that is, the portion where the power starts to be decreased).

In the optical portion of the multifocal contact lens, it is very important to dispose the distance portion and the near portion in a balanced manner with respect to a pupil. Therefore, it is important to keep a good balance between the distance portion and near portion, not only in the multi focal contact lens, but also in an ophthalmic lens including other contact lens or intraocular lens.

An object of the present invention is to keep a good balance between the near portion and the distance portion disposed at the outer edge of the near portion while ensuring the near dioptric power sufficiently in the near portion when the near portion is centrally disposed in the optical portion, and to keep a good balance between the distance portion and the near portion disposed at the outer edge of the distance portion while ensuring the distance dioptric power sufficiently in the distance portion when the distance portion is centrally disposed in the optical portion.

Means for Solving the Problem

In order to solve the above-described problem, and after a diligent study by the present inventors, it is found that the key to solving this problem is to eliminate the hatched portion in FIG. 2. The reason for generating the hatched portion in FIG. 2 is that the decrease of the power must already be started in the near portion when viewed in the X direction. Therefore, the present inventors obtain a technique of obtaining the near dioptric power at the end N of the near portion even if the decrease of the power starts in the near portion, by increasing the power more than the near dioptric power before start of the decrease of the power in the near portion as shown in FIG. 4(b). When the near portion is centrally disposed in this example, the near dioptric power is intensified (in a direction in which the nearer view can be seen, ie, in a positive direction, for example, 5.00D→5.10D), and thereafter the power may be decreased to the distance dioptric power, and conversely, when the distance portion is centrally disposed, the distance dioptric power is intensified (in a direction in which the far view can be seen, ie, in a negative direction, for example, 0.00D-0.10D), and then the power may be increased to the near dioptric power.

As a result of obtaining the above findings, the present inventors adopt a configuration of the present invention described below. The preferred embodiments described below can be combined as appropriate.

According to a first aspect of the present invention, there is provided an ophthalmic lens, including:

an optical portion having:

a near portion with a near dioptric power for viewing near distance; and a distance portion with a distance dioptric for viewing a distance further than the near distance;

with the near portion or the distance portion being centrally disposed, wherein a portion that is not centrally disposed is annularly disposed at an outer edge of the near portion or the distance portion, the near portion or the distance portion centrally disposed in the optical portion having a portion A in which power is intensified and then weakened when viewed in X direction from a center to a periphery, and having a portion A' in which power is intensified and then weakened when viewed in X' direction from the center to the periphery, which is an opposite direction to the X direction.

According to a second aspect of the present invention, there is provided the ophthalmic lens of the first aspect, wherein the near portion is centrally disposed in the optical portion, and in the portion A and the portion A', the power is intensified to nearer than the near dioptric power and then weakened to a distance dioptric power.

According to a third aspect of the present invention, there is provided the ophthalmic lens of the second aspect, wherein there is only one point where the power is locally maximum in the portion A, and there is only one point where the power is locally maximum in the portion A'.

According to a fourth aspect of the present invention, there is provided the ophthalmic lens of the second or third aspect, wherein a planar view distance between the portion where the power is locally maximum in the portion A and the portion where the power is locally maximum in the portion A' is 1.0 to 2.8 mm.

According to a fifth aspect of the present invention, there is provided the ophthalmic lens of any one of the second to fourth aspects, wherein a difference between a local maximum value of the power and the near dioptric power in the portion A is 0.05 to 0.25 D, and a difference between a local maximum value of the power and the near dioptric power in the portion A' is also 0.05 to 0.25D.

According to a sixth aspect of the present invention, there is provided the ophthalmic lens of the first aspect, wherein the distance portion is centrally disposed in the optical portion, and in the portion A and the portion A', the power is intensified to farther than the distance dioptric power and then weakened to a near dioptric power.

According to a seventh aspect of the present invention, there is provided the ophthalmic lens of the sixth aspect, wherein there is only one point where the power is locally minimum in the portion A, and there is only one point where the power is locally minimum in the portion A'.

According to an eighth aspect of the present invention, there is provided the ophthalmic lens of the sixth or the seventh aspect, wherein a planar view distance between the point where the power is locally minimum in the portion A and the point where the power is locally minimum in the portion A' is 1.0 to 2.8 mm.

According to a ninth aspect of the present invention, there is provided the ophthalmic lens of any one of the sixth to eighth aspects, wherein a difference between a local minimum value of the power and the distance dioptric power in the portion A is 0.05 to 0.25 D, and a difference between a local minimum value of the power and the distance dioptric power in the portion A' is also 0.05 to 0.25D.

According to a tenth aspect of the present invention, there is provided the ophthalmic lens of any one of the first to ninth aspects, wherein the ophthalmic lens is a contact lens (a soft contact lens or a hard contact lens, preferably the soft contact lens).

According to an eleventh aspect of the present invention, there is provided the ophthalmic lens of any one of the first to ninth aspects, wherein the ophthalmic lens is an intraocular lens.

According to a twelfth aspect of the present invention, there is provided a method for designing an ophthalmic lens including:

an optical portion having:

a near portion with a near dioptric power for viewing near distance;

and a distance portion with a distance dioptric for viewing a distance further than the near distance;

with the near portion or the distance portion being centrally disposed, wherein a portion that is not centrally disposed is annularly disposed at an outer edge of the near portion or the distance portion, and the near portion or the distance portion centrally disposed in the optical portion has a portion A in which power is intensified and then weakened when viewed in X direction from a center to a periphery, and has a portion A' in which power is intensified and then weakened when viewed in X' direction from the center to the periphery, which is an opposite direction to the X direction.

According to a thirteenth aspect of the present invention, there is provided the method of the twelfth aspect, wherein an ophthalmic lens is designed so that the near portion is centrally disposed in the optical portion, and in the portion A and the portion A', the power is intensified to nearer than the near dioptric power and then weakened to a distance dioptric power.

According to a fourteenth aspect of the present invention, there is provided the method of the thirteenth aspect, wherein there is only one point where the power is locally maximum in the portion A, and there is only one point where the power is locally maximum in the portion A'.

According to a fifteenth aspect of the present invention, there is provided the method of the thirteenth or the fourteenth aspect, wherein a planar view distance between the portion where the power is locally maximum in the portion A and the portion where the power is locally maximum in the portion A' is 1.0 to 2.8 mm.

According to a sixteenth aspect of the present invention, there is provided the method of any one of the thirteenth to fifteenth aspects, wherein a difference between a local maximum value of the power and the near dioptric power in the portion A is 0.05 to 0.25 D, and a difference between a local minimum value of the power and the near dioptric power in the portion A' is also 0.05 to 0.25D.

According to a seventeenth aspect of the present invention, there is provided the method of the twelfth aspect, wherein the distance portion is centrally disposed in the optical portion, and in the portion A and the portion A', the power is intensified farther than the distance dioptric power and then weakened to a near dioptric power.

According to an eighteenth aspect of the present invention, there is provided the method of the seventeenth aspect, wherein there is only one point where the power is locally minimum in the portion A, and there is only one point where the power is locally minimum in the portion A'.

According to a nineteenth aspect of the present invention, there is provided the method of the seventeenth or the eighteenth aspect, wherein a planar view distance between the portion where the power is locally minimum in the portion A and the portion where the power is locally minimum in the portion A' is 1.0 to 2.8 mm.

According to a twentieth aspect of the present invention, there is provided the method of any one of the seventeenth to nineteenth aspect, wherein a difference between a local minimum value of the power and the distance dioptric power in the portion A is 0.05 to 0.25 D, and a difference between a local minimum value of the power and the distance dioptric power in the portion A' is also 0.05 to 0.25D.

According to a twenty-first aspect of the present invention, there is provided the method of any one of the twelfth to twentieth aspects, wherein the ophthalmic lens is a contact lens (a soft contact lens or a hard contact lens, preferably the soft contact lens).

According to a twenty-second aspect of the present invention, there is provided the method of any one of the twelfth to twentieth aspect, wherein the ophthalmic lens is an intraocular lens.

According to a twenty-third aspect of the present invention, there is provided a method for manufacturing an ophthalmic lens, including designing an ophthalmic lens by the method for designing an ophthalmic lens according to any of the twelfth to twenty-second aspect; and manufacturing a designed ophthalmic lens by a processing device.

Further, an aspect of an ophthalmic lens set including a plurality of the above ophthalmic lenses is as follows. The above-described preferable aspects may be suitably combined to examples given as aspects of the present invention, etc., in this specification, can be suitably combined and can be included in the embodiment of the present application.

According to a twenty-fourth aspect of the present invention, there is provided an ophthalmic lens set including a plurality of ophthalmic lenses each including:

an optical portion having:

a near portion with a near dioptric power for viewing near distance; and a distance portion with a distance dioptric for viewing a distance farther than the near distance;

with the near portion or the distance portion being centrally disposed, wherein a portion that is not centrally disposed is annularly disposed at an outer edge of the near portion or the distance portion, and the near portion or the distance portion centrally disposed in the optical portion has a portion A in which power is intensified and then weakened when viewed in X direction from a center to a periphery, and having a portion A' in which power is intensified and then weakened when viewed in X' direction from the center to the periphery, which is an opposite direction to the X direction.

Further, the other aspects that can be combined with the above aspects are as follows.

According to a twenty-fifth aspect of the present invention, there is provided the ophthalmic lens set of each aspect, wherein the near portion is centrally disposed in the optical portion, and the portion A and the A' are the portions in which power is increased and then decreased (preferably the power continues to be decreased) to a near dioptric power or less, and then the power is decreased (preferably the power continues to be decreased) up to a distance dioptric power in the near portion.

According to a twenty-sixth aspect of the present invention, there is provided the ophthalmic lens set of the twenty-fifth aspect, wherein preferably there are two convex portions (ie, one concave portion) on an upper side when viewed in a power plot.

According to a twenty-seventh aspect of the present invention, there is provided the ophthalmic lens set of the twenty-fifth or twenty-sixth aspect, wherein the planar view distance is preferably 1.0 to 2.8 mm, a lower limit is more preferably 1.2 mm, still more preferably 1.4 mm, and very preferably 1.6 mm, and an upper limit is more preferably 2.6 mm, still more preferably 2.4 mm.

According to a twenty-eighth aspect of the present invention, there is provided the ophthalmic lens set of any one of the twenty-fifth to twenty-seventh aspect, wherein preferably a difference between a local maximum value of the power and a near dioptric power in portion A is 0.05 to 0.25 D, and a difference between a local maximum value of the power and a near dioptric power in portion A' is also 0.05 to 0.25 D. A lower limit of each is more preferably 0.10 D, further preferably 0.12 D, very preferably 0.15 D, and upper limit is more preferably 0.20D.

According to a twenty-seventh aspect of the present invention, there is provided the ophthalmic lens set of any one of the twenty-fifth to twenty-eighth aspect, wherein when a straight line X-X' is rotated from 0 to 180° around the optical center O with respect to a lens, a portion having a shape in which the power in the portion A and the portion A' is intensified to nearer than the near dioptric power and then weakened to the distance dioptric power, is preferably 50 area % or more, more preferably 80 area % or more, and further preferably 90 area % or more of an optical portion.

According to a thirtieth aspect of the present invention, there is provided the ophthalmic lens set of each aspect, wherein the distance portion is centrally disposed in the optical portion, and the portion A and the A' are the portions in which power is decreased and then increased (preferably the power continues to be increased) to the distance dioptric power or more, and then the power is increased (preferably the power continues to be increased) up to the near dioptric power, in the distance portion.

According to a thirty-first aspect of the present invention, there is provided the ophthalmic lens set of the thirtieth aspect, wherein preferably there are two concave portions (i.e., one convex portion on an upper side) when viewed in a power plot.

According to a thirty-second aspect of the present invention, there is provided the ophthalmic lens set of the thirtieth or thirty-first aspect, wherein the planar view distance is preferably 1.0 to 2.8 mm, a lower limit is more preferably 1.2 mm, still more preferably 1.4 mm, and very preferably 1.6 mm, and an upper limit is more preferably 2.6 mm, still more preferably 2.4 mm.

According to a thirty-third aspect of the present invention, there is provided the ophthalmic lens set of any one of the thirtieth to thirty-second aspects, wherein preferably a difference between a local minimum value of the power and the distance dioptric power in the portion A is 0.05 to 0.25 D, and a difference between a local minimum value of the power and the distance dioptric power in the portion A' is also 0.05 to 0.25 D. A lower limit of each is more preferably 0.10 D, further preferably 0.12 D, very preferably 0.15 D and an upper limit is more preferably 0.20 D.

According to a thirty-fourth aspect of the present invention, there is provided the ophthalmic lens set of any one of the thirtieth to thirty-third aspects, wherein when a straight line X-X' is rotated from 0 to 180° around the optical center O with respect to a lens, a portion having a shape in which the power in the portion A and the portion A' is intensified to farther than the distance dioptric power and then weakened to the near dioptric power, is preferably 50 area % or more, more preferably 80 area % or more, and further preferably 90 area % or more of the optical portion.

According to a thirty-fifth aspect of the present invention, there is provided the ophthalmic lens set of each aspect, wherein the ophthalmic lens is an intraocular lens, and the ophthalmic lens includes a lens body having the optical portion, and support portions extending from the lens body.

The support portions are, for example, two support portions extending in an arm shape from the lens body.

According to a thirty-sixth aspect of the present invention, there is provided an ophthalmic lens, a method for designing the same, and a method for manufacturing the same, the ophthalmic lens including a plurality of ophthalmic lenses each including:

an optical portion having:

a near portion with a near dioptric power for viewing near distance; and a distance portion with a distance dioptric for viewing a distance farther than the near distance;

with the near portion or the distance portion being centrally disposed, wherein a portion that is not centrally disposed is annularly disposed at an outer edge of the near portion or the distance portion, and the near portion or the distance portion centrally disposed in the optical portion has a portion A in which power is intensified and then weakened when viewed in X direction from a center to a periphery, and there is an inflection point of the power when viewed in X' direction from the center to the periphery, which is an opposite direction to the X direction.

Advantage of the Invention

According to the present invention, a good balance can be kept between the near portion and the distance portion disposed at the outer edge of the near portion while ensuring the near dioptric power sufficiently in the near portion when the near portion is centrally disposed in the optical portion, and a good balance can be kept between the distance portion and the near portion disposed at the outer edge of the distance portion while ensuring the distance dioptric power sufficiently in the distance portion when the distance portion is centrally disposed in the optical portion.

DETAILED DESCRIPTION OF THE INVENTION

Hereinafter, embodiments of the present invention will be described in detail with reference to the drawings. The present embodiment will be described in the following order.
1. Contact lens
1-1. Multifocal contact lens (multifocal lens)
1-1-1. Near portion is centrally disposed
1-1-2. Distance portion is centrally disposed
1-2. Other contact lens
2. Method for designing a contact lens (method for manufacturing the contact lens)
3. Intraocular lens (IOL) and a method for designing the same (method for manufacturing the same)
4. Ophthalmic lens set
5. Modified example Regarding a configuration which is not described below, a well-known configuration may be adopted suitably. Further, in the present specification, "to" refers to a predetermined value or more and a predetermined value or less. In addition, the ophthalmic lens mentioned here (lens body of a contact lens or an intraocular lens) has two surfaces facing each other. When a wearer wears the ophthalmic lens, one located on the retina side is referred to as "a back surface", and one located on the opposite object side is referred to as "a front surface".

Further, the term "power" refers to the power (in units of [D]) in the present specification.

As described above, when the near portion is centrally disposed, "the near dioptric power is intensified" refers to intensifying the power in a direction in which nearer view can be seen, that is, increasing the power in the positive direction (example: 5.00 D→5.10 D). Conversely, "the near dioptric power is weakened" refers to weakening the power in a direction in which the nearer view becomes difficult to see, that is, decreasing the power in a positive direction (example: 5.10 D→5.00 D).

On the other hand, when the distance portion is centrally disposed, "the distance dioptric power is intensified" refers to intensifying the power in a direction in which a distance view is seen, that is, increasing the power in a negative direction (example: 0.00 D→−0.10 D). Conversely, "the distance dioptric power is weakened" refers to weakening the power in a direction in which a distance view is difficult to see, that is, increasing the power in a positive direction (example: −0.10D→0.00D).

Namely, "the power is intensified" in a stage where which of the near portion or the distance portion is centrally disposed is unknown, refers to increasing the near dioptric power or the distance dioptric power, and "the power is weakened" refers to weakening the near dioptric power or the distance dioptric power.

1. Contact Lens

1-1. Multifocal Contact Lens (Multifocal Lens)

In the present embodiment, a multifocal contact lens (multifocal lens, hereinafter simply referred to as a lens) is mainly exemplified.

1-1-1. The Near Portion is Centrally Disposed

Figure 1:
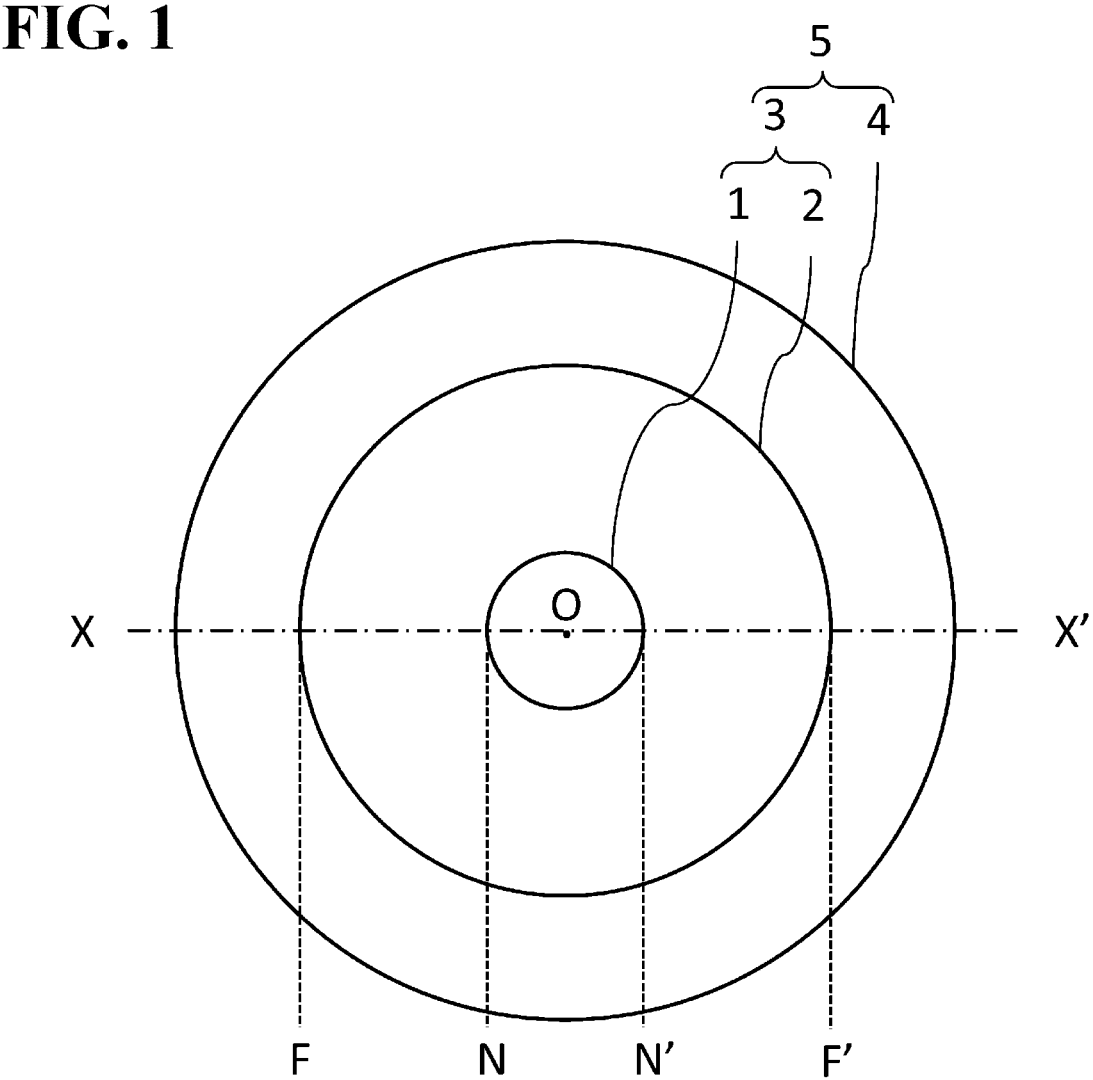
FIG. 1 is a schematic plan view of a conventional multifocal lens.

The lens in the present embodiment includes: a substantially circular optical portion mainly contributing to optical performance; and an annular peripheral portion disposed at the peripheral edge of the optical portion, similarly to the conventional lens described above. As described above, the peripheral portion usually has a flange shape that is easy to enter the back of an eyelid when the lens is placed on the cornea. Then, the optical portion includes: a near portion with a near dioptric power for viewing a near distance; and a distance portion with a distance dioptric power for viewing a distance (including infinity) farther than the near distance. Then, the present embodiment shows an example in which the near portion is centrally disposed and the distance portion is annularly disposed at the outer edge of the near portion. The configuration in plan view is the same as that in FIG. 1 described above. This example also shows an example of making the optical center O coincide with the geometric center of a lens. However, the present invention is not limited thereto (the same is applied hereafter).

The lens of this embodiment is different from the conventional one mainly in the plot of the power. Details will be described below.

Figure 2:
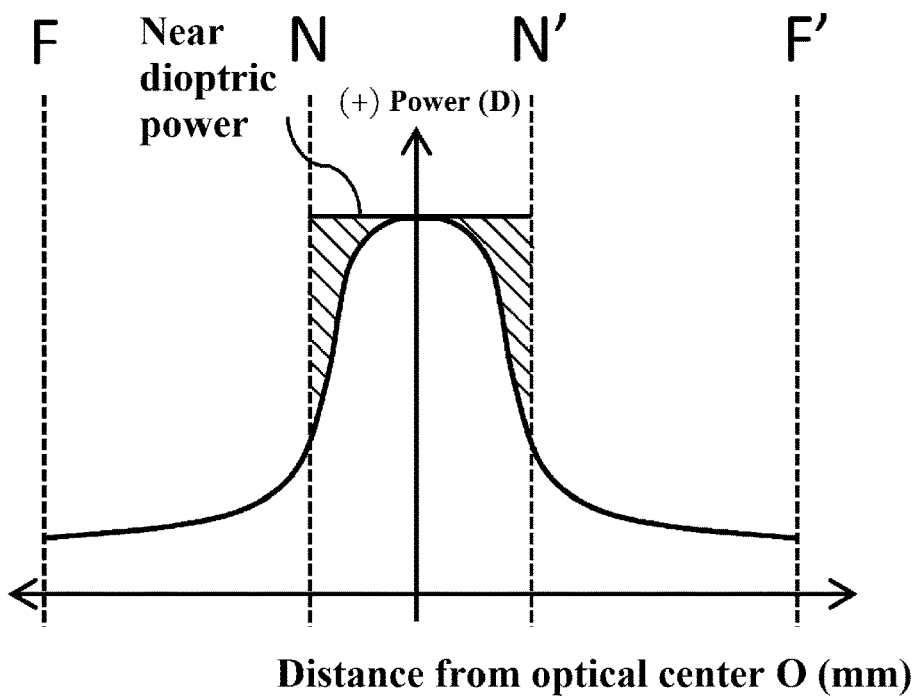
FIG. 2 is a power plot diagram, when the optical portion of the conventional multifocal contact lens is viewed from end F to end F' in X-X' direction.
Figure 3:
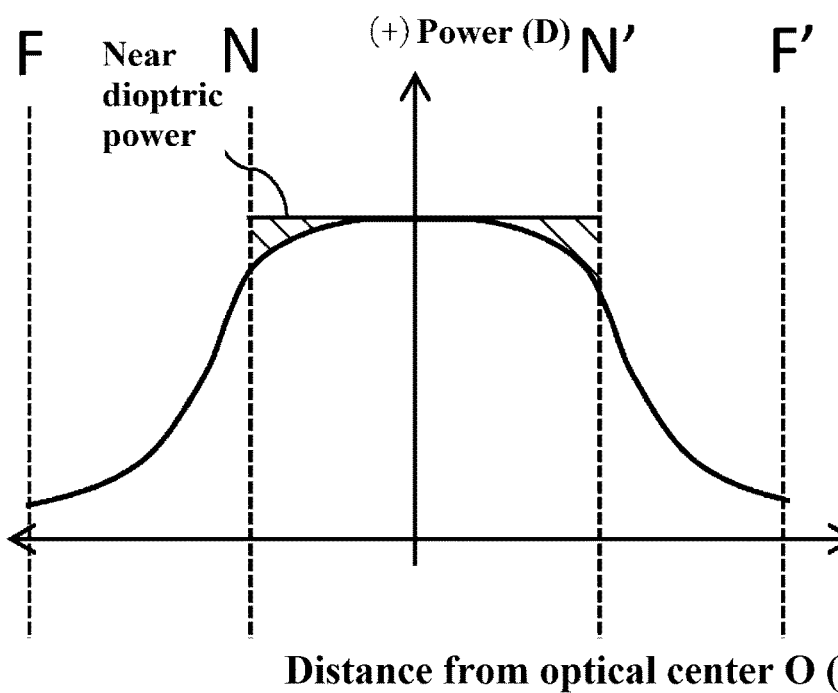
FIG. 3 is a diagram in which a position at which the power is decreased is away from an optical center O when viewed in X direction and X' direction.

The optical portion of the multifocal contact lens of the present embodiment will be described, using FIG. 4(*a*) which is a power plot diagram when the optical portion of the multifocal contact lens of the present embodiment is viewed from the end F to the end F' in the X-X' direction, and using FIG. 4 (*b*) which is an enlarged view of the near portion. Similarly to FIG. 2, the horizontal axis indicates the distance from the optical center O on the X-X' when the lens is viewed in plan. The vertical axis indicates a lens power (unit: diopter [D]).

As described above, the near portion is centrally disposed and the distance portion is annularly disposed at the outer edge of the near portion. Due to such a relationship, the power at the optical center O is set to be higher than the power in the distance portion. As a prescription of the lens, values of distance dioptric power S and addition diopter ADD (and astigmatism diopter C when performing astigmatism correction) are usually used, and the near dioptric power is the value of (S+ADD) (the unit of each power is [D], and the same is applied hereafter). The power in the vicinity of the optical center O in the near portion N-N' is set as the value of the near dioptric power. Strictly speaking, the power at the position of the optical center O is set as the value of the near dioptric power (ie, the power at the optical center O=near dioptric power), and meanwhile, when the optical center O deviates from the geometric center, the power at the geometric center may slightly deviate from the value of the near dioptric power.

Figure 4:
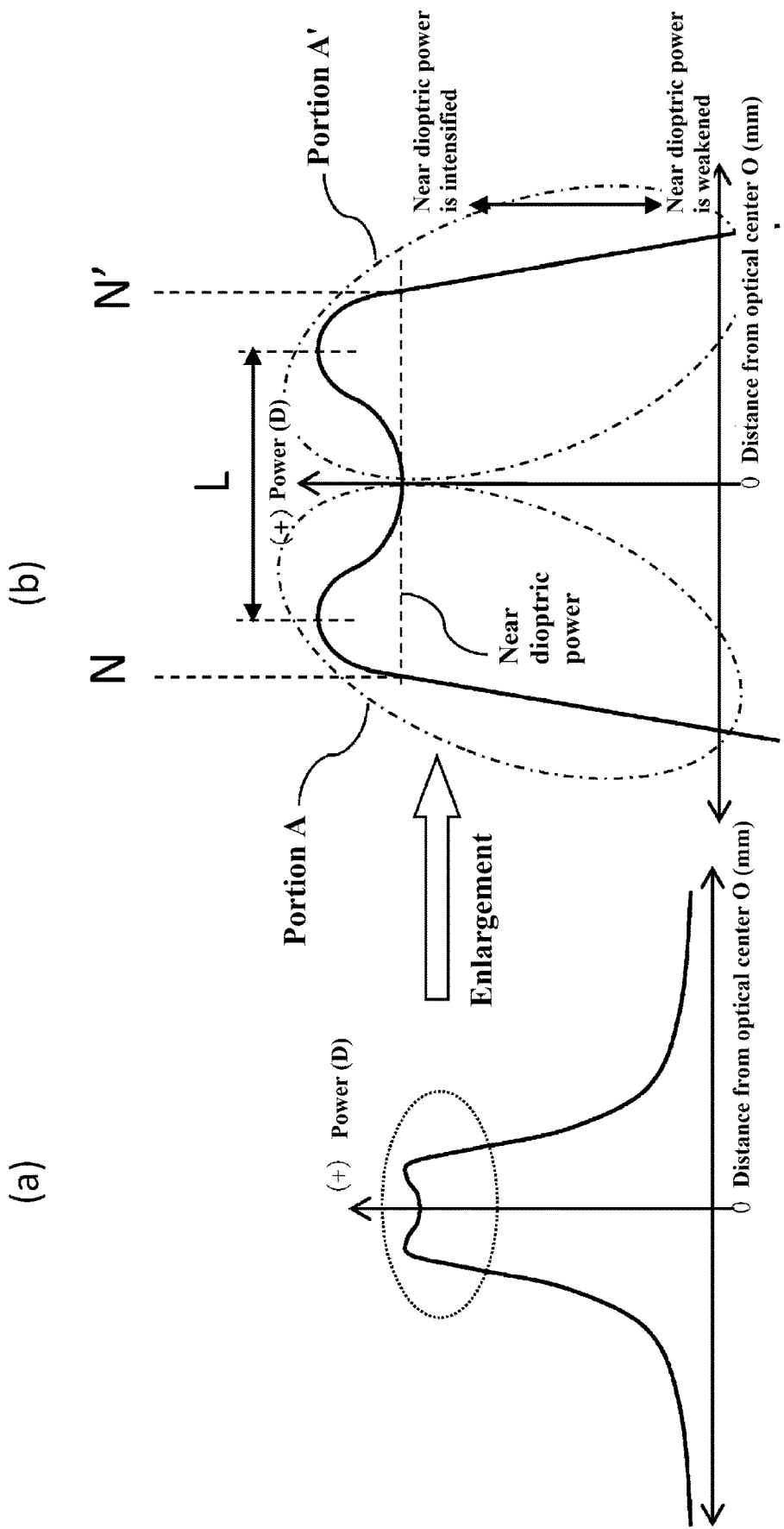
FIG. 4(a) is a power plot diagram when the optical part of the multifocal contact lens of the present embodiment is viewed from the end F to the end F' in the X-X' direction, and FIG. 4 (b) is an enlarged view of the near portion in FIG. 4 (a).

However, as shown in FIG. 4(*b*), the lens of the present embodiment has a shape in which the portion A and the portion A' have a shape in which the power is intensified to nearer than the near dioptric power and then weakened to a distance dioptric power. The portion A and the portion A' mentioned here refer to the following portions: for example in the portion A, power is increased and then decreased (preferably the power continues to be decreased) to a near dioptric power or less, and then the power is decreased (preferably the power continues to be decreased) up to a distance dioptric power in the near portion. Referring to FIG. 4, the portion A and the portion A' are the portions which exist in the near portion (center) but also exist in the distance portion which is the periphery thereof.

Preferably, there is only one point where the power is locally maximum in the portion A, and there is only one point where the power is locally maximum in the portion A'.

In other words, it is preferable that there are two convex portions (ie, one concave portion) on the upper side when viewed in the power plot. Due to this definition, it is not necessary to provide a large number of small convex portions when viewed in the power plot. Even if a large number of small convex portions are provided, it may be difficult to sufficiently fill the hatched portion shown in FIG. 2. Therefore, it is better to set a point where the power becomes locally maximum in the portion A and the portion A', as a largely occupying point on the power plot. However, this is not essential. For example, two or three local maximum points may also be provided.

Further, it is preferable that the planar view distance L between the point where the power is locally maximum in the portion A and the point where the power is locally maximum in the portion A' is 1.0 to 2.8 mm. The lower limit is more preferably 1.2 mm, still more preferably 1.4 mm, and very preferably 1.6 mm, and the upper limit is more preferably 2.6 mm, still more preferably 2.4 mm. This definition makes it possible to ensure that the position where the power is increased and then decreased is appropriate. However, this is not essential, and the planar view distance L may be appropriately set according to the type of the lens.

Further, preferably, the difference between the local maximum of the power and the near dioptric power in the portion A is 0.05 to 0.25 D, and also preferably, the difference between the local maximum of the power and the near dioptric power in the portion A' is 0.05 to 0.25 D. The lower limit of each is more preferably 0.10 D, more preferably 0.12 D, very preferably 0.15 D, and the upper limit of each is more preferably 0.20D. This definition makes it possible to fill the hatched portion shown in FIG. 2 sufficiently and reliably. However, this is not essential, and the above difference may be set appropriately according to a situation, and of course, the above power difference may be different between the portion A and the portion A'.

In the present embodiment, there is a great characteristic in the behavior of the increase and decrease of the power in the portion centrally disposed (here, the near portion). Due to this characteristic, it is possible to ensure that a portion disposed at the outer edge (here the distance portion) is wide enough. Therefore, the power plot of the distance portion on the outer edge is not particularly limited. For example, the distance portion on the outer edge may have the power plot as shown in FIG. 4(a), namely, may have the power plot in which the power is decreased gradually at the beginning, then is decreased sharply, and the decrease of the power becomes gradual again, and continues to decrease even after reaching the distance dioptric power in the end.

Figure 5:
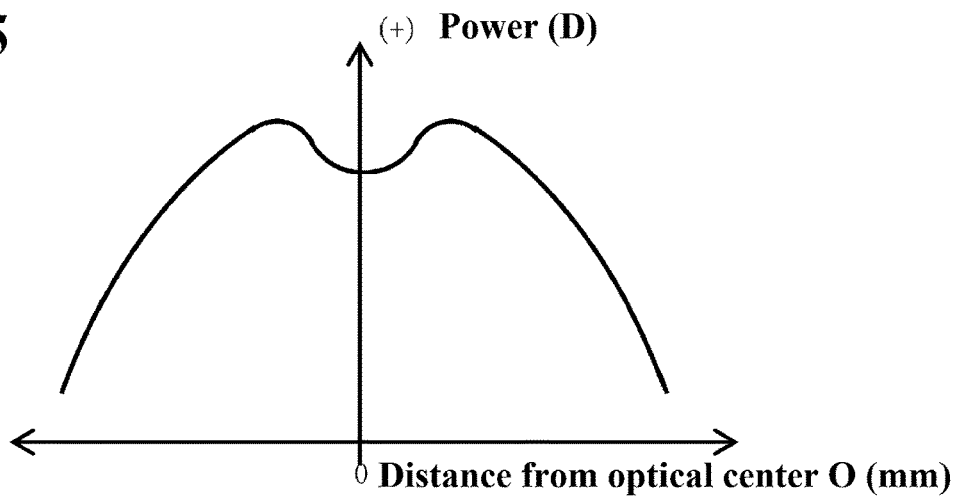
FIG. 5 is a power plot diagram of another pattern in the multifocal contact lens of the present embodiment.

On the other hand, as shown in FIG. 5, the distance portion may also have the power plot in which the power is decreased gradually at the beginning, and then the power continues to decrease even after a little bit sharp decrease and reaches the distance dioptric power in the end.

Figure 6:
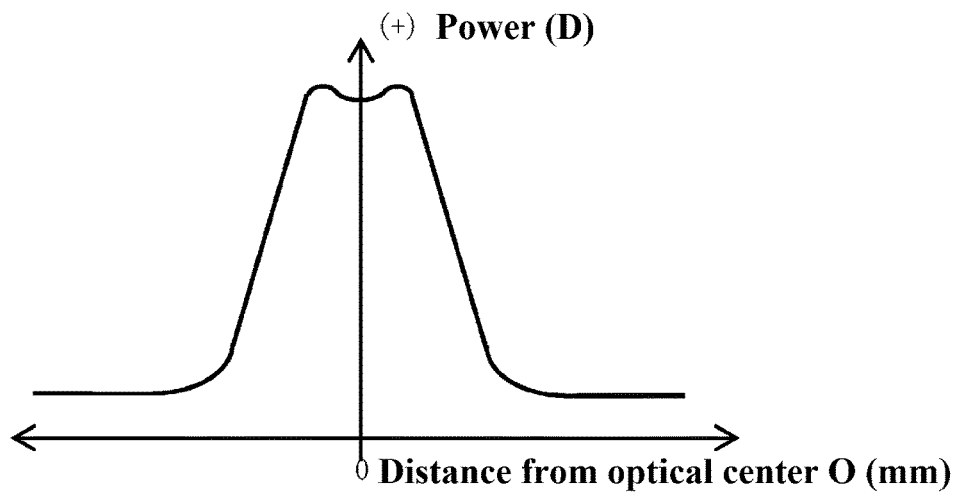
FIG. 6 is a power plot diagram of another pattern in the multifocal contact lens of the present embodiment.

Further, as shown in FIG. 6, the distance portion may also have the power plot in which the power is decreased gradually at the beginning, and then the power is decreased sharply, and the decrease of the power becomes gradual again, and after the power reaches the distance dioptric power in the end, the power variation disappears.

Figure 7:
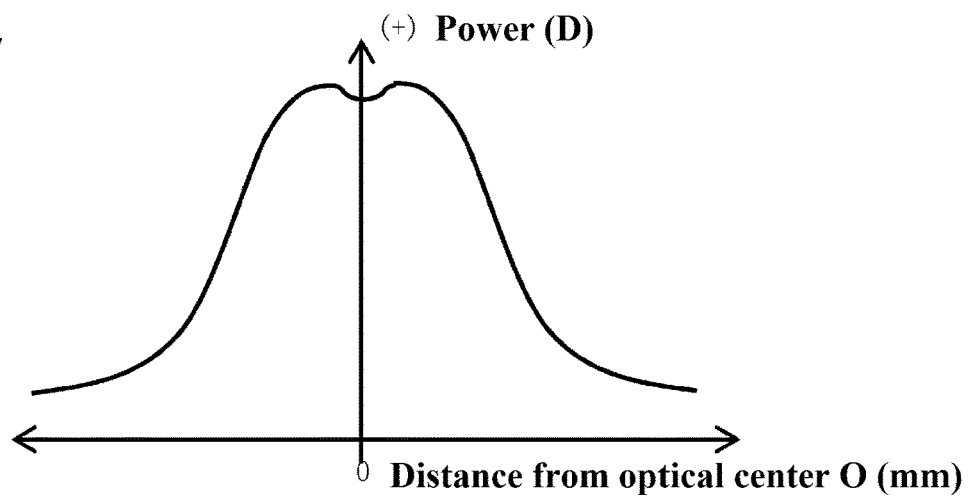
FIG. 7 is a power plot diagram of another pattern in the multifocal contact lens of the present embodiment.

Further, as shown in FIG. 7, the distance portion may also have the power plot in which the power is decreased gradually at the beginning, and then the power continues to decrease even after a little bit sharp decrease and reaches the distance dioptric power in the end.

Further, the present invention does not exclude a case of providing an annular near portion at the further peripheral edge, in addition to centrally disposing the near portion, and peripherally disposing the distance portion. Further, although it will be described in detail later, the same applies to the case where the distance portion is centrally disposed, the near portion at the peripheral edge of the distance portion, and the annular distance portion is disposed at the further peripheral edge of the near portion.

In the above description, the near portion in this embodiment is defined by the power plot. However, it is also possible to define the near portion by the shape (curvature) of the front surface instead of the power plot. This is because in the case of a conventional lens, the surface (rear surface) in contact with the cornea must be shaped according to a surface (for example, a spherical surface or a toric surface) conforming to the shape of the cornea. In this case, it is necessary to adjust the power according to the shape of an eyelid-side surface (front surface). As a result, the characteristic of the power plot can also be represented by the shape (curvature) of the front surface of the lens, and the following ophthalmic lens can be provided. Namely, there is provided an ophthalmic lens, including:

an optical portion having:

a near portion with a near dioptric power for viewing near distance; and a distance portion with a distance dioptric power for viewing a distance further than the near distance;

with the near portion or the distance portion being centrally disposed, wherein a portion that is not centrally disposed is annularly disposed at an outer edge of the near portion or the distance portion, the near portion or the distance portion centrally disposed in the optical portion having a portion A in which a radius of curvature is decreased and then increased when viewed in X direction from a center to a periphery, and having a portion A' in which the radius of curvature is decreased and then increased when viewed in X' direction from the center to the periphery, which is an opposite direction to the X direction.

Preferably, there is only one point where a radius of curvature is locally minimum in the portion A, and there is only one point where a radius of curvature is locally minimum in the portion A'.

Preferably, a planar view distance between the point where the radius of curvature is locally minimum in the portion A and the point where the radius of curvature is locally minimum in the portion A' is 1.0 to 2.8 mm.

Preferably, a suitable value of the difference between the local minimum value of the radius of curvature in the portion A and the radius of curvature at the optical center is largely due to a central power (power), and is for example 0.01 to 0.13 mm, preferably 0.03 to 0.11 mm, and the difference between the local minimum value of the radius of curvature and the near dioptric power in the portion A' is also, for example, 0.01 to 0.13 mm, preferably 0.03 to 0.11 mm. At this time, the power at the optical center is −3.00 D, a base curve is 8.5 mm, a refractive index is 1.45, and a center thickness is 0.10 mm.

Incidentally, a suitable example in the case of using the power can also be applied to the case of using the radius of curvature, provided that the power is converted to the radius of curvature.

The lens of the present embodiment has a shape in which the power in the portion A and the portion A' is intensified to nearer than the near dioptric power and then weakened to the distance dioptric power. For example, when the straight line X-X' is rotated from 0 to 180° around the optical center O with respect to a lens, the portion having the above shape is preferably 50 area % or more, more preferably 80 area % or more, and further preferably 90 area % or more of an entire body of the optical portion (For convenience of explanation, it is also simply referred to as an optical portion).

In the present specification, "area %" means a percentage of a total area of the portions having the above shape (for example, two fan-shaped portions surrounded by the optical center O and the arc of the outermost edge of the optical portion (portion A at 0° to 180°, portion A' at 180° to 360°)) in plan view, with respect to the area of the optical portion similarly in plan view.

Further, as described above, although there is not a visually identifiable boundary between the optical portion and the peripheral portion of the lens, it can be identified by using a device (power meter) that measures the power of the lens.

1-1-2. Distance Portion is Centrally Disposed

Figure 8:
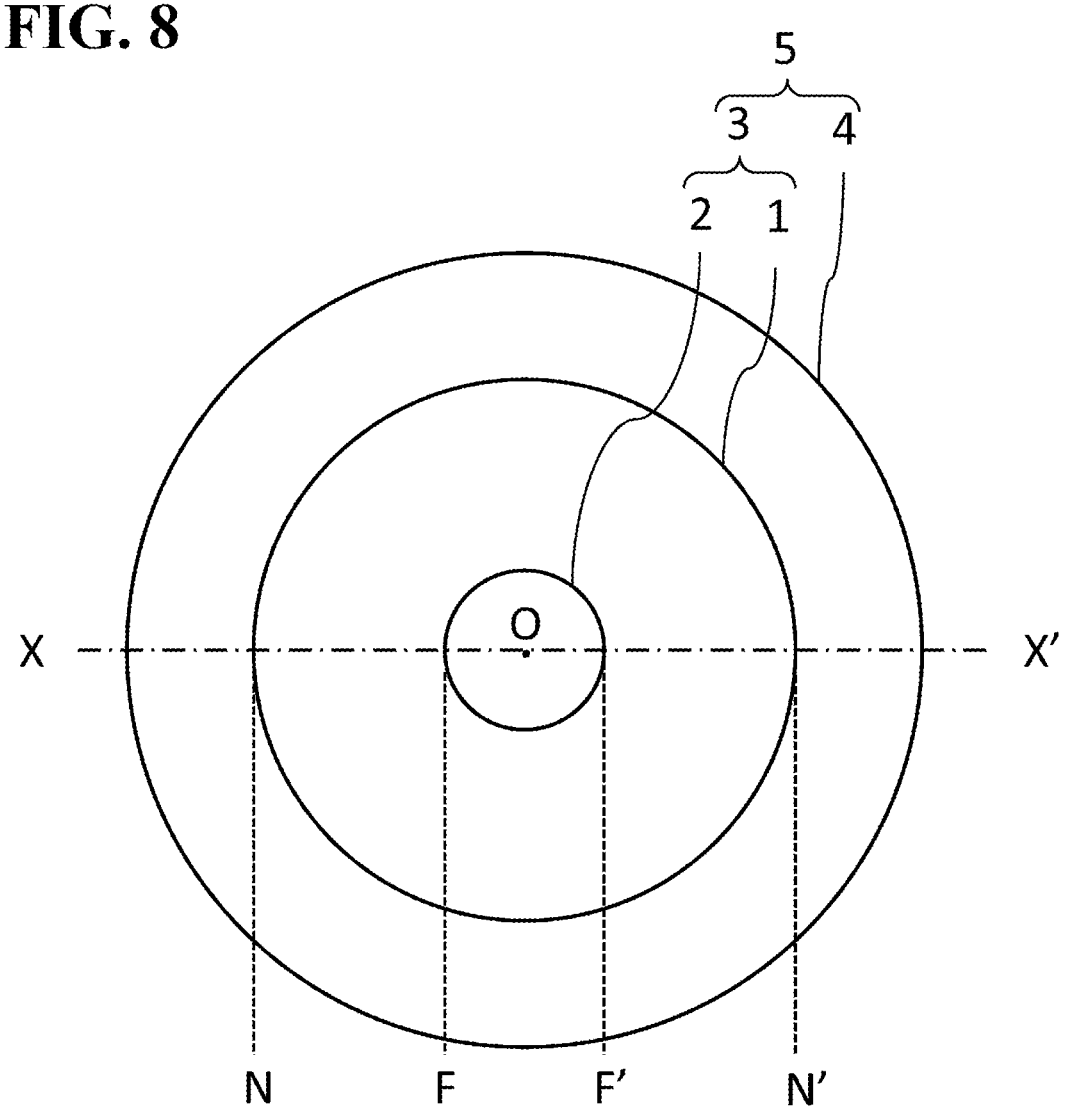
FIG. 8 is a schematic view of a multifocal lens (centrally disposing a distance portion and disposing a near portion at the outer edge of the distance portion) as a planar view.

Contrary to the above example, the idea of the present invention can also be applied to a case where the distance portion is centrally disposed and the near portion is annularly disposed at the outer edge of the distance portion. The configuration in plan view is obtained by reversing the positions of the near portion and the distance portion in FIG. 4 described above. FIG. 8 shows such a state.

Figure 9:
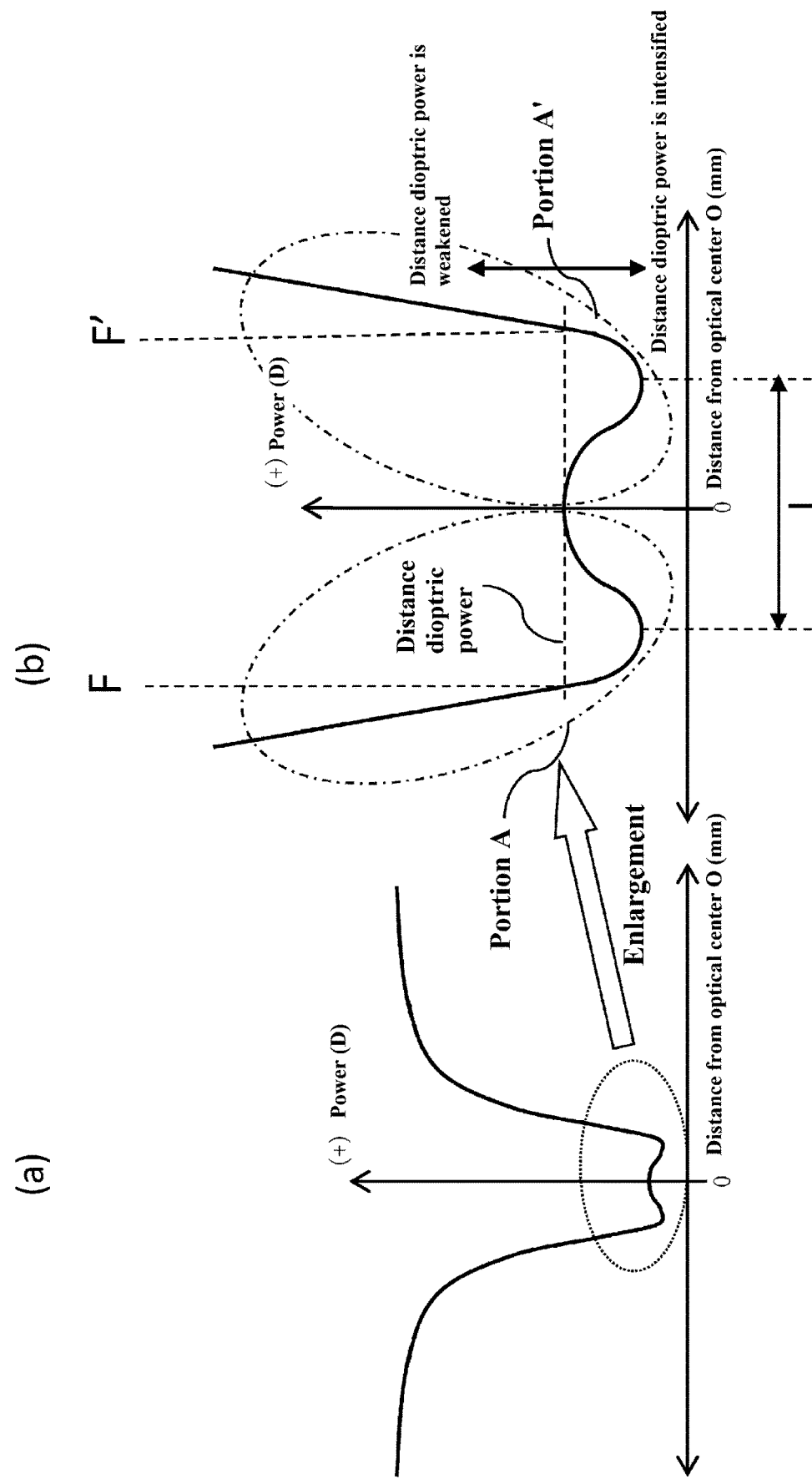
FIG. 9 (a) is a power plot diagram when the optical portion of the multifocal contact lens of another embodiment is viewed from end N end N' in the X-X' direction, and FIG. 9 (b) is an enlarged view of a distance portion in FIG. 9 (a).

The portion A and the portion A' in this example are the portions in which power is decreased and then increased (preferably the power continues to be increased) to the distance dioptric power or more, and then the power is increased (preferably the power continues to be increased) up to the near dioptric power in the distance portion. Referring to FIG. 9, the portion A and the portion A' are the portions which exist in the distance portion (center) but also exist in the near portion which is the periphery thereof.

The optical portion of the multifocal contact lens of this example will be described, using FIG. 9 (a) which is a power plot diagram when the optical portion of the multifocal contact lens of this example is viewed from end N end N' in the X-X' direction, and FIG. 9 (b) which is an enlarged view of the distance portion.

In this example, the distance portion is centrally disposed and the near portion is annularly disposed at the outer edge of the distance portion. Due to such a relationship, the power at the optical center O is set to be lower than the power in the near portion. As a prescription of the lens, values of the distance dioptric power S and addition diopter ADD (and astigmatism diopter C when performing astigmatism correction) are usually used. Strictly speaking, the power at the position of the optical center O is set as the value of the distance dioptric power (ie, the power at the optical center O=distance dioptric power S), and meanwhile, when the optical center O deviates from the geometric center, the power at the geometric center may slightly deviate from the value of the distance dioptric power.

However, as shown in FIG. 9(b), the lens of this example has a shape in which in the portion A and the portion A', the power is intensified to farther than the distance dioptric power (intensified in a direction of a farther view, that is, in a negative direction) and then weakened to the near dioptric power (weakened in a direction of not enabling the farther view, that is, weakened from the negative direction).

Preferably, there is only one point where the power is locally minimum in the portion A, and there is only one point where the power is locally minimum in the portion A'. In other words, it is preferable that there are two concave portions (ie, one convex portion) on the upper side when viewed in the power plot. Due to this definition, it is not necessary to provide a large number of small concave portions when viewed in the power plot. Even if a large number of small concave portions are provided, it may be difficult to ensure sufficient distance dioptric power. Therefore, it is better to set a point where the power becomes locally minimum in the portion A and the portion A', as a largely occupying point on the power plot. However, this is not essential. For example, two or three local maximum points may be provided.

Further, it is preferable that the planar view distance L between the point where the power is locally minimum in the portion A and the point where the power is locally minimum in the portion A' is 1.0 to 2.8 mm. The lower limit is more preferably 1.2 mm, still more preferably 1.4 mm, and very preferably 1.6 mm, and the upper limit is more preferably 2.6 mm, still more preferably 2.4 mm. This definition makes it possible to ensure that the position where the power is increased and then decreased is appropriate. However, this is not essential, and the planar view distance L may be appropriately set according to the type of lens.

Further, preferably, the difference between the local minimum value of the power and the distance dioptric power in the portion A is 0.05 to 0.25 D, and also preferably, the difference between the local minimum value of the power and the distance dioptric power in the portion A' is 0.05 to 0.25 D. The lower limit of each is more preferably 0.10 D, more preferably 0.12 D, very preferably 0.15 D, and the upper limit of each is more preferably 0.20D. This definition makes it possible to fill the hatched portion shown in FIG. 2 sufficiently and reliably. However, this is not essential, and the above difference may be set appropriately according to a situation, and of course, the above power difference may be different between the portion A and the portion A'.

In this example as well, there is a great characteristic in the behavior of the increase and decrease of the power centrally disposed (here, the distance portion). Due to this characteristic, it is possible to ensure that a portion disposed at the outer edge (here the near portion) is wide enough. Therefore, the power plot of the near portion on the outer edge is not particularly limited. For example, the shape of the power plot of FIGS. 5 to 7 shown above may be reversed upside down.

The lens of this example has a shape in which the power is intensified to farther than the distance dioptric power and then weakened to the near dioptric power in the portion A and the portion A'. For example, when the straight line X-X' is rotated from 0 to 180° around the optical center O with respect to a lens, a portion having the above shape is preferably 50 area % or more, more preferably 80 area % or more, and further preferably 90 area % or more of the optical portion.

Further, also in the case of defining the distance portion by the shape (curvature) of the front surface instead of the power plot, the principle is the same as described above in the case of centrally disposing the near portion, and the near portion and the distance portion may be interchanged, the local maximum may be replaced with the local minimum, and "(the radius of curvature is decreased and then increased)" may be replaced with "(the radius of curvature is increased and then decreased)".

1-2. Other Contact Lens

In the present embodiment, the multifocal contact lens is exemplified. However, a technical idea of the present invention can be applied to other contact lens.

For example, a bifocal contact lens has the following configuration: in the case of centrally disposing the near portion, there is a portion A in which the power is intensified to nearer than the near dioptric power and then weakened to a distance dioptric power when viewed in X direction from the center to the periphery, and there is a portion A' in which power is intensified to nearer than the near dioptric power and then weakened to the distance dioptric power when viewed in X' direction from the center to the periphery, which is the opposite direction to the X direction. This makes it possible to keep a good balance between the near portion and the distance portion provided at the outer edge of the near portion, while ensuring a sufficient near dioptric power in the near portion. Regarding preferred example etc., it will be omitted because it overlaps with the contents described in the section of <1-1-1. The near portion is centrally disposed>.

The technical idea of the present invention can also be applied to the case of centrally disposing the distance portion and disposing the near portion at the outer edge of the distance portion. Regarding the content thereof, it will be omitted because it overlaps with the contents described in the section of <1-1-2. The distance portion is centrally disposed>.

Further, also in the multifocal contact lens, the toric shape does not prevent the above-described behavior of the power, and therefore the technical idea of the present invention can be applied thereto.

The lens of the present embodiment including the portions A and A' described above can be applied whether it is a soft contact lens or a hard contact lens. However, the soft contact lens with little movement on the cornea is more preferable in providing sufficient optical performance and customer satisfaction with a wearer.

As a result of the above, according to each example of the present embodiment, it becomes possible to keep a good balance between the near portion and the distance portion provided at the outer edge of the near portion while sufficiently ensuring the near dioptric power in the near portion when the near portion is centrally disposed in the optical portion, and it becomes possible to keep a good balance between the distance portion and the near portion provided at the outer edge of the distance portion while sufficiently ensuring the distance dioptric power in the distance portion when the distance portion is centrally disposed in the optical portion.

2. Method for Designing a Contact Lens (Method for Manufacturing the Contact Lens)

The above contents can be sufficiently applied to a method for designing and manufacturing a contact lens. For example, the method for designing a contact lens is as follows.

"There is provided a method for designing an ophthalmic lens including:

an optical portion having:

a near portion with a near dioptric power for viewing near distance; and a distance portion with a distance dioptric for viewing a distance further than the near distance;

with the near portion or the distance portion being centrally disposed, wherein a portion that is not centrally disposed is annularly disposed at an outer edge of the near portion or the distance portion, and the near portion or the distance portion centrally disposed in the optical portion has a portion A in which power is intensified and then weakened when viewed in X direction from a center to a periphery, and has a portion A' in which power is intensified and then weakened when viewed in X' direction from the center to the periphery, which is an opposite direction to the X direction."

Regarding a specific design method, it is sufficient to design using a known lens design method or a design apparatus. Further, division into cases of (centrally disposing the near portion and centrally disposing the distance portion) described in <1. Contact lens>, and each preferred example can also be applied to <2. Method for designing a contact lens (method for manufacturing the contact lens)>. Therefore, the description is omitted here because it overlaps with the description of the <1. Contact lens>.

Further, the method for manufacturing a contact lens includes: a designing step of designing an ophthalmic lens according to the above-described method for designing an ophthalmic lens (the respective preferred examples are appropriately combined in some cases); and a processing step of manufacturing the designed ophthalmic lens with a processing device. Regarding a specific processing method, it is sufficient to perform processing using a lens processing device which is also known.

3. Intraocular Lens (IOL) and a Method for Designing the Same (Method for Manufacturing the Same)

The technical idea of the present invention can be sufficiently applied to an intraocular lens (IOL) and a method for designing (method for manufacturing) the same. There is no limitation in particular as an intraocular lens, and the technical idea of the present invention can be applied to an intraocular lens of a type (in-the-bag) placed in a lens capsule, an intraocular lens of a type (out-the-bag) placed outside the capsule, an intraocular lens of a sewing type, and the like.

When the technical idea of the present invention is applied to the intraocular lens, at least an optical portion may be required. As described in <1-1. Multifocal contact lens (multifocal lens)>, an annular peripheral portion may be provided on the peripheral edge of the optical portion mainly contributing to the optical performance. However, the intraocular lens of the present example described here includes the optical portion and the support portions for supporting the optical portion in the lens capsule. A relatively large case is the case where the intraocular lens includes the above-described optical portion and the support portions extending from the optical portion. For the support portions, the shape of the support portions of the known intraocular lens may be adopted. However, two support portions extending in an arm shape from the optical portion may be provided in the optical portion and a lens having such a configuration may be used as an intraocular lens.

Regarding the method for designing an intraocular lens (the method for manufacturing an intraocular lens), description thereof is omitted because it is the same as the design described in <2. Method for designing a contact lens (method for manufacturing an intraocular lens)>. Regarding a specific method for designing an intraocular lens (method for manufacturing an intraocular lens), it is sufficient to perform the design using a known method (processing device) for designing an intraocular lens. Further, division into cases of (centrally disposing the near portion and centrally disposing the distance portion) described in <1. Contact lens>, and each preferred example can also be applied to <2. Method for designing a contact lens (method

4. Ophthalmic Lens Set

The above-described content can be sufficiently applied to the contact lens set including a plurality of contact lenses exemplified in the present embodiment, and the intraocular lens set including a plurality of intraocular lenses similarly exemplified in the present embodiment. These lens sets are collectively referred to as "an ophthalmic lens set".

When selling at least a contact lens as a product, multiple contact lenses with a wide variety of powers and base curves (Example: Multiple contact lenses with the same base curve but different powers) are collectively sold frequently as one trade name, as well as selling one contact lens.

Therefore, the technical idea of the present invention is sufficiently reflected on the ophthalmic lens set including a plurality of lenses exhibiting the behavior of power such as power of the contact lens (or intraocular lens etc.) of the present embodiment described in detail above.

From a different perspective, it is found that all the ophthalmic lens sets constituting the ophthalmic lens set in the present embodiment exhibit the behavior of the power as described above. This shows that, even if one ophthalmic lens showing the above behavior of power is produced in the conventional art, the composition is completely different between the ophthalmic lens thus produced by chance and the ophthalmic lens set of this embodiment.

The configuration of the ophthalmic lens set including a plurality of the above ophthalmic lenses is as follows. For the following configuration, the above-described preferred examples may be suitably combined.

There is provided an ophthalmic lens set including a plurality of ophthalmic lenses each including:

an optical portion having:

a near portion with a near dioptric power for viewing near distance; and a distance portion with a distance dioptric for viewing a distance farther than the near distance;

with the near portion or the distance portion being centrally disposed, wherein a portion that is not centrally disposed is annularly disposed at an outer edge of the near portion or the distance portion, and the near portion or the distance portion centrally disposed in the optical portion has a portion A in which power is intensified and then weakened when viewed in X direction from a center to a periphery, and having a portion A' in which power is intensified and then weakened when viewed in X' direction from the center to the periphery, which is an opposite direction to the X direction.

5. Modified Example

The present invention is not limited to the above examples, and the above examples and preferred examples may, of course, be combined as appropriate. Further, in the above-described embodiment, the ophthalmic lens has the portions in which power is intensified and then weakened in both the X direction and the X' direction. However, it is expected that the effect of the present invention can be exhibited more or less even if only one of the portions is present. The contents are as follows.

"There is provided an ophthalmic lens, a method for designing the same, and a method for manufacturing the same, the ophthalmic lens including a plurality of ophthalmic lenses each including:

an optical portion having:

a near portion with a near dioptric power for viewing near distance; and a distance portion with a distance dioptric for viewing a distance farther than the near distance;

with the near portion or the distance portion being centrally disposed, wherein a portion that is not centrally disposed is annularly disposed at an outer edge of the near portion or the distance portion, and the near portion or the distance portion centrally disposed in the optical portion has a portion A in which power is intensified and then weakened when viewed in X direction from a center to a periphery, and there is an inflection point of the power when viewed in X' direction from the center to the periphery, which is an opposite direction to the X direction."

By the way, the reason for the existence of the inflection point of the power in the X' direction is as follows: the effect of the present invention is exhibited easily in a case of a shape close to the shape of intensifying and then weakening the power in the X' direction, although not completely the same shape. And the expression that defines the shape close to the above shape is defined by the expression such that "the inflection point of the power exists".

EXAMPLE

Next, the present invention will be specifically described by way of examples. Of course, the present invention is not limited to the following examples.

A soft contact lens (simply referred to as a lens hereafter) which is the multifocal contact lens according to the present invention, and a lens according to the conventional art (which does not reflect the technical idea of the present invention), were prepared, and a test was conducted with a 50's male as a subject. A lens according to the present invention at this time was referred to as example 1, and a lens according to the conventional art was referred to as comparative example 1.

Further, separately from the above test, a 60's male was used as a subject, and a test was conducted using each of the above lenses. A lens according to the present invention at this time was referred to as example 2, and a lens according to the conventional art was referred to as comparative example 2.

Example 1, Comparative Example 1

First, a full correction value was set for the 50's male. The term "full correction value" means a condition under which the subject can most easily see an object. The full correction value in right eye (VD) and left eye (VS) is shown below.

VD=1.5×S+0.50 D (effective addition power+1.20 D in consideration of a vertex distance)

VS=1.5×S+0.50 D (effective addition power+1.20 D in consideration of the vertex distance)

The meaning of each of the above formulas is such that the visual acuity of 1.5 can be achieved by setting the spherical power S to 0.50D. Further, the effective addition power+1.20 D in consideration of the vertex distance shows a correction amount when the case of the vertex distance 12 mm in the spectacle lens, corresponds to the case of the contact lens.

Further, the prescription of the lens of example 1 and comparative example 1 is as follows.
R: BC 8.7 mm/P+0.50 D/ADD+1.50 (A lens in which the near portion is centrally disposed and the distance portion is disposed at the periphery of the near portion in the optical portion)
L: BC 8.7 mm/P+0.50 D/ADD+1.50 (lens in which the near portion is centrally disposed and the distance portion is disposed at the periphery of the near portion in the optical portion)

Figure 10:
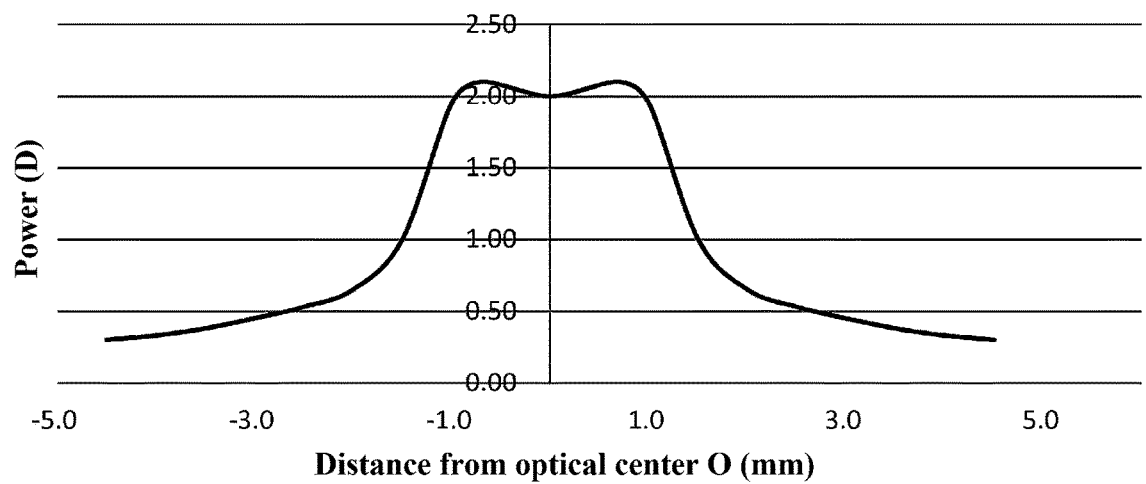
FIG. 10 is a power plot diagram when the optical portion of the lens of example 1 is viewed from end F to the end F' in the X-X' direction.

FIG. 10 is a power plot diagram when the optical portion of the lens of example 1 is viewed from end F to end F' in the X-X' direction. Further, in the lens of example 1, when the straight line X-X' is rotated from 0 to 180° around the optical center O with respect to the lens, the optical portion (entire body) is made to have the above shape.

Figure 11:
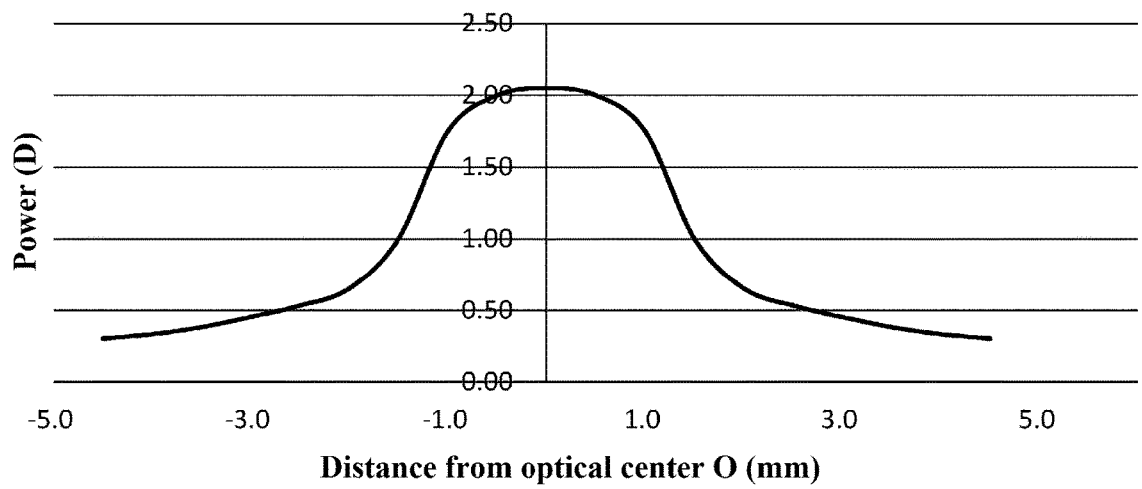
FIG. 11 is a power plot diagram when the optical portion of the lens of comparative example 1 is viewed from the end F to the end F' in the X-X' direction.

Similarly, FIG. 11 is a power plot diagram when the optical portion of the lens of comparative example 1 is viewed from the end F to the end F' in the X-X' direction. The results are shown in Table 1 below.

TABLE 1

|  | Example 1 | Comparative example 1 |
| --- | --- | --- |
| Distance view | ○ (Satisfactory) | ○ (Satisfactory) |
| Near view | ○ (Satisfactory) | x (Unsatisfactory) |

As shown in Table 1, in Example 1, a subject could be satisfied in both distance vision and near vision. On the other hand, in Comparative Example 1, the subject could not be satisfied in the near vision. The reason can be considered as follows: the near dioptric power is insufficient due to narrowing of the near portion, in other words, the distance portion is excessively ensured in order to ensure the distance dioptric power.

Example 2, Comparative Example 2

First, the full correction value was set for 60s male. The term "full correction value" means a condition under which the subject can most easily see the object. The full correction value in right eye (VD) and left eye (VS) is shown below.
VD=1.5×S-1.25D (effective addition power+1.80D in consideration of the vertex distance)
VS=1.5×S-1.25D (effective addition power+1.80D in consideration of the vertex distance)

Further, a prescription of the lens of Example 2 and Comparative Example 2 is as follows.
R: BC 8.7 mm/P-1.25 D/ADD+2.00 (a lens in which the near portion is centrally disposed and the distance portion is disposed at the periphery of the near portion, in the optical portion)
L: BC 8.7 mm/P-1.25 D/ADD+2.00 (A lens in which the near portion is centrally disposed and the distance portion is disposed at the periphery of the near portion, in the optical portion)

Figure 12:
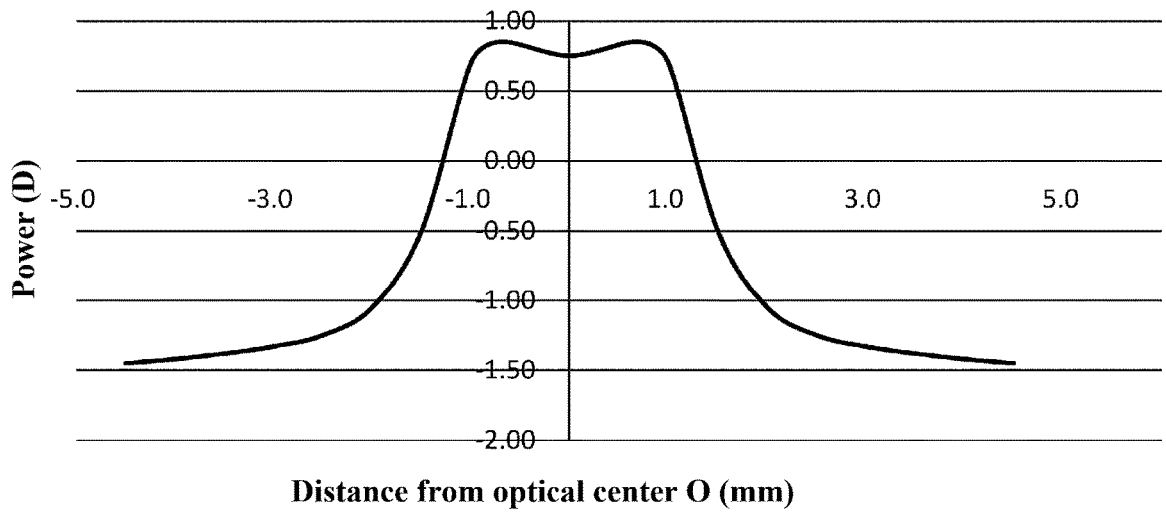
FIG. 12 is a power plot diagram when the optical portion of the lens of example 2 is viewed from the end F to the end F' in the X-X' direction.

FIG. 12 is a power plot diagram when the optical portion of the lens of example 2 is viewed from the end F to the end F' in the X-X' direction. Further, the optical portion (entire body) is configured to have the above shape when the straight line X-X' is rotated from 0 to 180° around the optical center O with respect to the lens.

Figure 13:
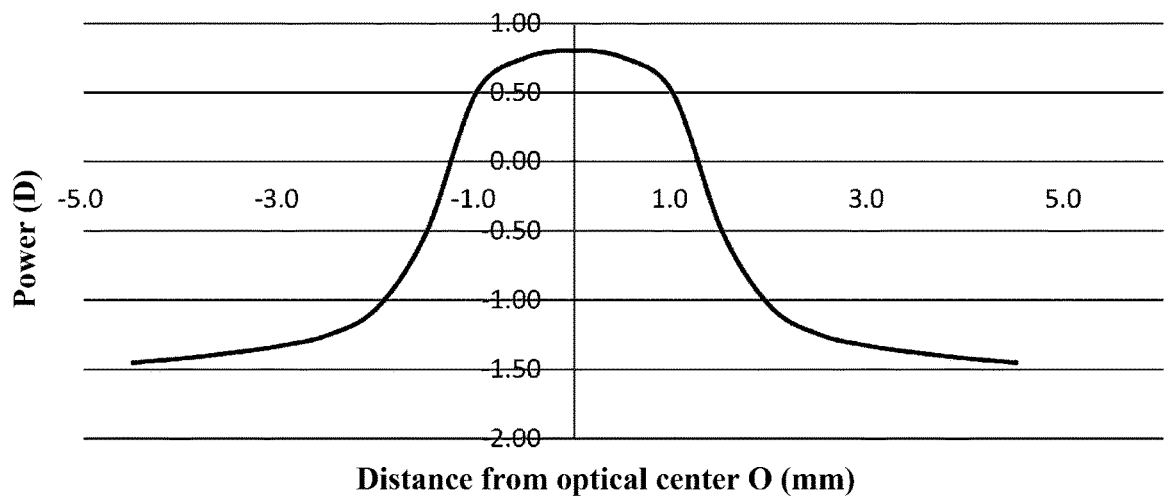
FIG. 13 is a power plot diagram when the optical portion of the lens of comparative example 2 is viewed from the end F to the end F' in the X-X' direction.

Similarly, FIG. 13 is a power plot diagram when the optical portion of the lens of Comparative Example 2 is viewed from the end F to the end F' in the X-X' direction. The results are shown in Table 2 below.

TABLE 2

|  | Example 2 | Comparative example 2 |
| --- | --- | --- |
| Distance view | ○ (Satisfactory) | ○ (Satisfactory) |
| Near view | ○ (Satisfactory) | x (Unsatisfactory) |

As shown in Table 2, in Example 2, the subject could be satisfied in both distance vision and near vision. On the other hand, in Comparative Example 2, the subject could not be satisfied in the near vision as well. In the same way as Comparative Example 1, the reason can be considered as follows: the near dioptric power is insufficient due to narrowing of the near portion, in other words, the distance portion is excessively ensured in order to ensure the distance dioptric power.

CONCLUSION

The above results reveal the fact that according to each example, when the near portion is centrally disposed in the optical portion, it is possible to keep a good balance between the near portion and the distance portion provided at the outer edge of the near portion while ensuring the near dioptric power sufficiently in the near portion. The same effect can be sufficiently expected when the distance portion is centrally disposed in the optical portion.

DESCRIPTION OF SINGS AND NUMERALS

1 Near portion
2 Distance portion
3 Optical portion
4 Peripheral portion
5 Multifocal contact lens

The invention claimed is:
1. An ophthalmic lens, comprising:
an optical portion having:
a near portion with a near dioptric power for viewing near distance; and
a distance portion with a distance dioptric power for viewing a distance further than the near distance; wherein
the near portion or the distance portion is centrally disposed at a center of the optical portion,
the distance portion or the near portion that is not disposed at the center of the optical portion is annularly disposed at an outer edge of the near portion or the distance portion that is disposed at the center of the optical portion and has constant or substantially constant dioptric power, and
the near portion or the distance portion disposed at the center of the optical portion has a portion A in which power is intensified and then weakened when viewed in X direction from the center to a periphery, and has a portion A' in which power is intensified and then weakened when viewed in X' direction from the center to the periphery, which is an opposite direction to the X direction.
2. The ophthalmic lens according to claim 1, wherein the near portion is centrally disposed in the optical portion, and in the portion A and the portion A', the power is intensified to nearer than the near dioptric power and then weakened to a distance dioptric power.

3. The ophthalmic lens according to claim 2, wherein there is only one point where the power is locally maximum in the portion A, and there is only one point where the power is locally maximum in the portion A'.

4. The ophthalmic lens according to claim 2, wherein a planar view distance between the portion where the power is locally maximum in the portion A and the portion where the power is locally maximum in the portion A' is 1.0 to 2.8 mm.

5. The ophthalmic lens according to claim 2, wherein a difference between a local maximum value of the power and the near dioptric power in the portion A is 0.05 to 0.25 D, and a difference between a local maximum value of the power and the near dioptric power in the portion A' is also 0.05 to 0.25D.

6. The ophthalmic lens according to claim 1, wherein the distance portion is centrally disposed in the optical portion, and in the portion A and the portion A', the power is intensified to farther than the distance dioptric power and then weakened to a near dioptric power.

7. The ophthalmic lens according to claim 6, wherein there is only one point where the power is locally minimum in the portion A, and there is only one point where the power is locally minimum in the portion A'.

8. The ophthalmic lens according to claim 6, wherein a planar view distance between the point where the power is locally minimum in the portion A and the point where the power is locally minimum in the portion A' is 1.0 to 2.8 mm.

9. The ophthalmic lens according to claim 6, wherein a difference between a local minimum value of the power and the distance dioptric power in the portion A is 0.05 to 0.25 D, and a difference between a local minimum value of the power and the distance dioptric power in the portion A' is also 0.05 to 0.25D.

10. The ophthalmic lens according to claim 1, wherein the ophthalmic lens is a contact lens.

11. The ophthalmic lens according to claim 1, wherein the ophthalmic lens is an intraocular lens.

12. A method for designing an ophthalmic lens comprising:
an optical portion having:
a near portion with a near dioptric power for viewing near distance; and
a distance portion with a distance dioptric power for viewing a distance further than the near distance; wherein
the near portion or the distance portion is centrally disposed at a center of the optical portion,
the distance portion or the near portion that is not disposed at the center of the optical portion is annularly disposed at an outer edge of the near portion or the distance portion that is disposed at the center of the optical portion and has constant or substantially constant dioptric power, and
and the near portion or the distance portion disposed at the center of the optical portion has a portion A in which power is intensified and then weakened when viewed in X direction from the center to a periphery, and has a portion A' in which power is intensified and then weakened when viewed in X' direction from the center to the periphery, which is an opposite direction to the X direction.

13. The method for designing an ophthalmic lens according to claim 12, wherein an ophthalmic lens is designed so that the near portion is centrally disposed in the optical portion, and in the portion A and the portion A', the power is intensified to nearer than the near dioptric power and then weakened to a distance dioptric power.

14. The method for designing an ophthalmic lens according to claim 13, wherein there is only one point where the power is locally maximum in the portion A, and there is only one point where the power is locally maximum in the portion A'.

15. The method for designing an ophthalmic lens according to claim 14, wherein a planar view distance between the portion where the power is locally maximum in the portion A and the portion where the power is locally maximum in the portion A' is 1.0 to 2.8 mm.

16. The method for designing an ophthalmic lens according to claim 13, wherein a difference between a local minimum value of the power and the near dioptric power in the portion A is 0.05 to 0.25 D, and a difference between a local minimum value of the power and the near dioptric power in the portion A' is also 0.05 to 0.25D.

17. The method for designing an ophthalmic lens according to claim 12, wherein the distance portion is centrally disposed in the optical portion, and in the portion A and the portion A', the power is intensified farther than the distance dioptric power and then weakened to a near dioptric power.

18. The method for designing an ophthalmic lens according to claim 17, wherein there is only one point where the power is locally minimum in the portion A, and there is only one point where the power is locally minimum in the portion A'.

19. The method for designing an ophthalmic lens according to claim 18, wherein a planar view distance between the portion where the power is locally minimum in the portion A and the portion where the power is locally minimum in the portion A' is 1.0 to 2.8 mm.

20. The method for designing an ophthalmic lens according to claim 17, wherein a difference between a local minimum value of the power and the distance dioptric power in the portion A is 0.05 to 0.25 D, and a difference between a local minimum value of the power and the distance dioptric power in the portion A' is also 0.05 to 0.25D.

21. The method for designing an ophthalmic lens according to claim 12, wherein the ophthalmic lens is a contact lens.

22. The method for designing an ophthalmic lens according to claim 12, wherein the ophthalmic lens is an intraocular lens.

23. A method for manufacturing an ophthalmic lens, comprising:
designing an ophthalmic lens by the method for designing an ophthalmic lens according to claim 12; and
manufacturing a designed ophthalmic lens by a processing device.

24. An ophthalmic lens set including a plurality of ophthalmic lenses each including:
an optical portion having:
a near portion with a near dioptric power for viewing near distance; and
a distance portion with a distance dioptric power for viewing a distance farther than the near distance; wherein
the near portion or the distance portion is centrally disposed at a center of the optical portion,
the distance portion or the near portion that is not disposed at the center of the optical portion is annularly disposed at an outer edge of the near portion or the distance portion that is disposed at the center of the optical portion and has constant or substantially constant dioptric power, and the near portion or the distance portion disposed at the center of the optical portion has a portion A in which power is intensified and then weakened when viewed in X direction from the center to a periphery, and has a portion A' in which power is intensified and then weakened when viewed in X' direction from the center to the periphery, which is an opposite direction to the X direction.

* * * * *